United States Patent
He et al.

(10) Patent No.: US 12,295,792 B2
(45) Date of Patent: May 13, 2025

(54) METHOD, APPARATUS AND DEVICE FOR CALCULATING SIGNAL ATTENUATION, AND COMPUTER-READABLE STORAGE MEDIUM

(71) Applicant: WUXI HISKY MEDICAL TECHNOLOGIES CO., LTD., Jiangsu (CN)

(72) Inventors: Qiong He, Jiangsu (CN); Jinhua Shao, Jiangsu (CN); Jin Sun, Jiangsu (CN); Houli Duan, Jiangsu (CN)

(73) Assignee: Wuxi Hisky Medical Technologies Co., Ltd., Jiangsu (CN)

( * ) Notice: Subject to any disclaimer, the term of this patent is extended or adjusted under 35 U.S.C. 154(b) by 589 days.

(21) Appl. No.: 17/631,098

(22) PCT Filed: Jul. 28, 2020

(86) PCT No.: PCT/CN2020/105008
§ 371 (c)(1),
(2) Date: Jan. 28, 2022

(87) PCT Pub. No.: WO2021/018102
PCT Pub. Date: Feb. 4, 2021

(65) Prior Publication Data
US 2022/0249063 A1    Aug. 11, 2022

(30) Foreign Application Priority Data
Aug. 1, 2019   (CN) .......................... 201910706619.7

(51) Int. Cl.
*A61B 8/00* (2006.01)
*G01N 29/11* (2006.01)
(Continued)

(52) U.S. Cl.
CPC .......... *A61B 8/5207* (2013.01); *A61B 8/5223* (2013.01); *G01N 29/11* (2013.01); *G01N 29/38* (2013.01); *G01N 29/4418* (2013.01)

(58) Field of Classification Search
USPC ....................................................... 702/189
See application file for complete search history.

(56) References Cited

U.S. PATENT DOCUMENTS 5,524,626 A * 6/1996 Liu ..................... G01S 7/52049
                                                           600/442
2012/0127200 A1  5/2012 Kohara et al.
(Continued)

FOREIGN PATENT DOCUMENTS

CN          102743226 A          10/2012
CN          105930665 A           9/2016
(Continued)

OTHER PUBLICATIONS

Kak, A., Dines, K. Signal Processing of Broadband Pulsed Ultrasound: Measurement of Attenuation of Soft Biological Tissues. IEEE Transactions on Biomedical Engineering [online]. vol. BME-25, No. 4, pp. 321-344, Jul. 1978. Retrieved from the Internet: <https://ieeexplore.ieee.org/>. (Year: 1978).*

(Continued)

*Primary Examiner* — Paul D Lee
(74) *Attorney, Agent, or Firm* — SALIWANCHIK, LLOYD & EISENSCHENK (57) ABSTRACT

Disclosed are a method, apparatus and device for calculating signal attenuation, and a computer-readable storage medium. The method comprises: receiving an ultrasound signal by an ultrasonic imaging system, performing signal recovery operation on the ultrasound signal propagating in a tissue to obtain a recovered ultrasound signal; determining a type of the recovered ultrasound signal, and calculating attenuation information of the recovered ultrasound signal by adopting a calculation mode corresponding to the type according to the type of the recovered ultrasound signal. As such, the signal attenuation calculation flow is simplified, thereby enabling use of commercial probes therein, bringing convenience in operation, and increasing applicability. Accuracy and efficiency of attenuation calculation can be improved by means of performing signal recovery on an obtained ultrasonic signal and then performing attenuation calculation thereon.

7 Claims, 3 Drawing Sheets

(51) Int. Cl.
*G01N 29/38* (2006.01)
*G01N 29/44* (2006.01)

(56) References Cited

U.S. PATENT DOCUMENTS

| | | | |
|---|---|---|---|
| 2015/0071516 A1 | 3/2015 | Kim | |
| 2016/0331352 A1* | 11/2016 | Kawashima | A61B 8/5269 |
| 2016/0367225 A1* | 12/2016 | Ichikawa | A61B 8/14 |
| 2017/0119253 A1* | 5/2017 | Suehira | A61B 8/4416 |
| 2017/0258438 A1* | 9/2017 | Kanayama | A61B 8/5207 |

FOREIGN PATENT DOCUMENTS

| | | |
|---|---|---|
| CN | 108720870 A | 11/2018 |
| CN | 110313940 A | 10/2019 |

OTHER PUBLICATIONS

Kim, H., Varghese, T. Attenuation Estimation Using Spectral Cross-Correlation. IEEE Transactions on Ultrasonics, Ferroelectrics, and Frequency Control [online]. vol. 54, No. 3, pp. 510-519, Mar. 2007. Retrieved from the Internet: < https://ieeexplore.ieee.org/>. (Year: 2007).*

* cited by examiner

METHOD, APPARATUS AND DEVICE FOR CALCULATING SIGNAL ATTENUATION, AND COMPUTER-READABLE STORAGE MEDIUM

CROSS REFERENCE TO RELATED APPLICATIONS

This application is a National Stage of International Application No. PCT/CN2020/105008, filed on Jul. 28, 2020, which claims priority to Chinese Patent Application No. 201910706619.7, filed on Aug. 1, 2019; both of which are hereby incorporated by reference in their entireties.

TECHNICAL FIELD

The present disclosure relates to the field of data processing, and in particular to a method, apparatus and device for calculating signal attenuation and a computer-readable storage medium.

BACKGROUND

When a signal is propagating in a transmission medium, part of energy thereof is converted into heat energy or absorbed by the transmission medium, causing the signal to continuously decline in strength, which is called "attenuation". For an ultrasound signal, it is necessary to calculate attenuation thereof in order to carry out an analysis thereof.

In the prior art, in order to calculate attenuation of an ultrasound signal, signal attenuation of an upper surface and a lower surface of a detected object is generally calculated with standard probes.

The aforementioned signal attenuation calculation method, however, can only be implemented with standard probes instead of commonly used commercial probes. As a result, the method has disadvantages such as high demands on hardware, complex operation and strict experimental conditions, which are unfavorable to use.

SUMMARY

The present disclosure provides a method, apparatus and device for calculating signal attenuation and a computer-readable storage medium, which are used for solving the technical problem that the conventional ultrasound signal attenuation calculation method has the disadvantages of high demands on hardware, complex operation and strict experimental conditions, which are unfavorable to use.

A first aspect of the present disclosure provides a method for calculating signal attenuation, which comprises:
receiving an ultrasound signal propagating in a tissue;
performing signal recovery operation on the ultrasound signal propagating in a tissue to obtain a recovered ultrasound signal; and
determining a type of the recovered ultrasound signal, and calculating attenuation information of the recovered ultrasound signal by adopting a calculation mode corresponding to the type according to the type of the recovered ultrasound signal.

Another aspect of the present disclosure provides an apparatus for calculating signal attenuation, which comprises:
an acquisition module, configured for receiving an ultrasound signal propagating in a tissue;
a recovery module, configured for performing signal recovery operation on the ultrasound signal propagating in a tissue to obtain a recovered ultrasound signal; and
a calculation module, configured for determining a type of the recovered ultrasound signal and calculating attenuation information of the recovered ultrasound signal by adopting a calculation mode corresponding to the type according to the type of the recovered ultrasound signal.

Yet another aspect of the present disclosure provides a device for calculating signal attenuation, which comprises: a memory and a processor, wherein
the memory is configured for storing instructions executable by the processor; and
the processor is configured for executing the method for calculating signal attenuation as described above.

Yet another aspect of the present disclosure provides a computer-readable storage medium having computer-executable instructions stored thereon, wherein the computer-executable instructions are used to implement the method for calculating signal attenuation as described above when executed by a processor.

According to the method, apparatus and device for calculating signal attenuation and the computer-readable storage medium provided by the present disclosure, an ultrasound signal propagating in a tissue is received; signal recovery operation is performed on the ultrasound signal propagating in a tissue to obtain a recovered ultrasound signal; the type of the recovered ultrasound signal is determined, and attenuation information of the recovered ultrasound signal is calculated by adopting a calculation mode corresponding to the type according to the type of the recovered ultrasound signal. Thereby, the signal attenuation calculation flow is simplified, enabling use of commercial probes therein, bringing convenience in operation, and increasing applicability. In addition, the accuracy and efficiency of attenuation calculation can be increased by performing attenuation calculation subsequent to the recovery of the acquired ultrasound signal.

BRIEF DESCRIPTION OF THE DRAWINGS

In order to more clearly illustrate the embodiments of the present disclosure or the technical solutions in the prior art, the drawings which need to be used in the description of the embodiments or the prior art will be briefly described below. Apparently, the drawings in the following descriptions are some embodiments of the present disclosure, and other drawings can also be obtained by those of ordinary skill in the art according to these drawings.

DETAILED DESCRIPTION

In order to make the objective, technical solution and advantages of the present disclosure clearer, the technical solutions in the embodiments of the present disclosure will be clearly and completely described below with reference to the drawings in the embodiments of the present disclosure. Apparently, the embodiments described are merely part of the embodiments of the present disclosure, rather than all the embodiments. All other embodiments obtained based on the embodiments in the present disclosure shall fall within the protection scope of the present disclosure.

When a signal is propagating in a transmission medium, part of energy thereof is converted into heat energy or absorbed by the transmission medium, causing the signal to continuously decline in strength, which is called "attenuation". For an ultrasound signal, it is necessary to calculate attenuation of the ultrasound signal needs to be analyzed. In order to calculate the attenuation of the ultrasound signal, the signal attenuation of the upper surface and the lower surface of a detected object is generally calculated by standard probes in the prior art. However, the aforementioned signal attenuation calculation method can only be implemented by the standard probes instead of commonly used commercial probes, and as a result, the method has the disadvantages of high demands on hardware, complex operation and strict experimental conditions, which are unfavorable to use. In order to solve the aforementioned technical problem, the present disclosure provides a method, apparatus and device for calculating signal attenuation and a computer-readable storage medium.

It should be noted that the method, apparatus and device for calculating signal attenuation and the computer-readable storage medium provided by the present application may be applied to a scenario where attenuation calculation is performed on any signal.

Figure 1:
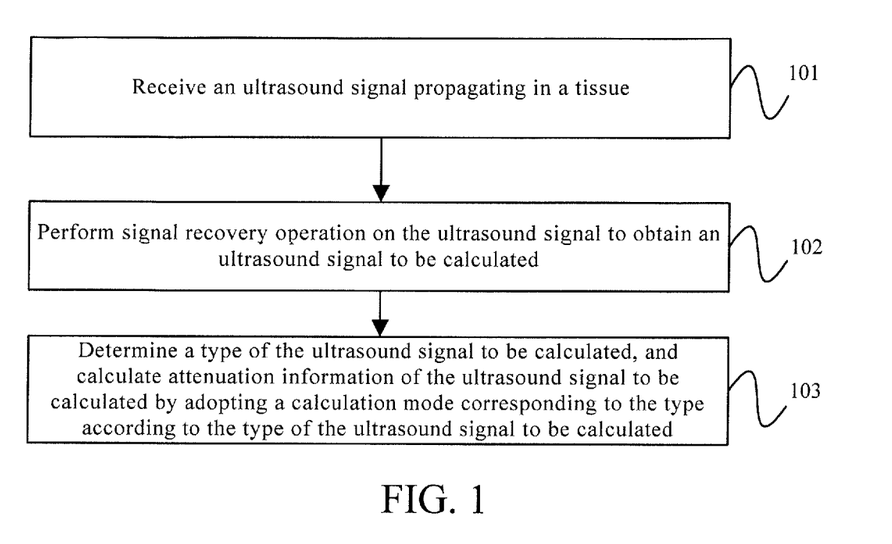
FIG. 1 is a schematic flowchart of a method for calculating signal attenuation according to Embodiment 1 of the present disclosure.

FIG. 1 is a schematic flowchart of a method for calculating signal attenuation according to Embodiment 1 of the present disclosure. As shown in FIG. 1, the method comprises:

Step 101: receiving an ultrasound signal propagating in a tissue;

Step 102: performing signal recovery operation on the ultrasound signal to obtain an ultrasound signal to be calculated, i.e., a recovered ultrasound signal; and Step 103: determining a type of the ultrasound signal to be calculated, and calculating attenuation information of the ultrasound signal to be calculated by adopting a calculation mode corresponding to the type according to the type of the ultrasound signal to be calculated.

This embodiment is executed by an apparatus for calculating signal attenuation. For an ultrasound signal, it is necessary to calculate attenuation thereof in order to carry out an analysis thereof. Therefore, the ultrasound signal for which attenuation information needs to be calculated needs to be acquired first; and particularly, the acquisition of the ultrasound signal may be implemented by an ultrasound imaging system. In order to focus on a partial region, generally, settings, such as probe focusing or system gain, are adopted. As a result, attenuation information obtained by calculating an ultrasound signal based on probe focusing or system gain is often not accurate enough. In order to increase the accuracy of signal attenuation information, after the ultrasound signal is obtained, signal recovery operation needs to be performed on the ultrasound signal to obtain an ultrasound signal to be calculated. It can be understood that there are two different types of ultrasound signals to be calculated, i.e. a time-domain signal and a frequency-domain signal. In order to ensure the accuracy of attenuation information calculation, different calculation modes should be adopted for respective different types of ultrasound signals to be calculated. Therefore, after an ultrasound signal to be calculated is obtained, the type of the ultrasound signal to be calculated needs to be determined first, then a calculation mode corresponding to the signal type is adopted according to the different types, and the ultrasound signal to be calculated is calculated by the calculation mode corresponding to the signal type, so that attenuation information corresponding to the ultrasound signal is obtained. Optionally, the ultrasound signal may be a one-dimensional ultrasound signal, a two-dimensional ultrasound signal or a three-dimensional ultrasound signal, which is not limited herein. Alternatively, the ultrasound signal may be either of a reflection signal and a transmission signal, which is not limited herein.

According to the method for calculating signal attenuation provided by this embodiment, an ultrasound signal is acquired by an ultrasound imaging system; signal recovery operation is performed on the ultrasound signal to obtain an ultrasound signal to be calculated; the type of the ultrasound signal to be calculated is determined, and attenuation information of the ultrasound signal to be calculated is calculated by adopting a calculation mode corresponding to the type according to the type of the ultrasound signal to be calculated. Thereby, the signal attenuation calculation flow is simplified, enabling use of commercial probes therein, bringing convenience in operation, and increasing applicability. In addition, the accuracy and efficiency of attenuation calculation can be increased by performing attenuation calculation subsequent to the recovery of the acquired ultrasound signal.

Figure 2:
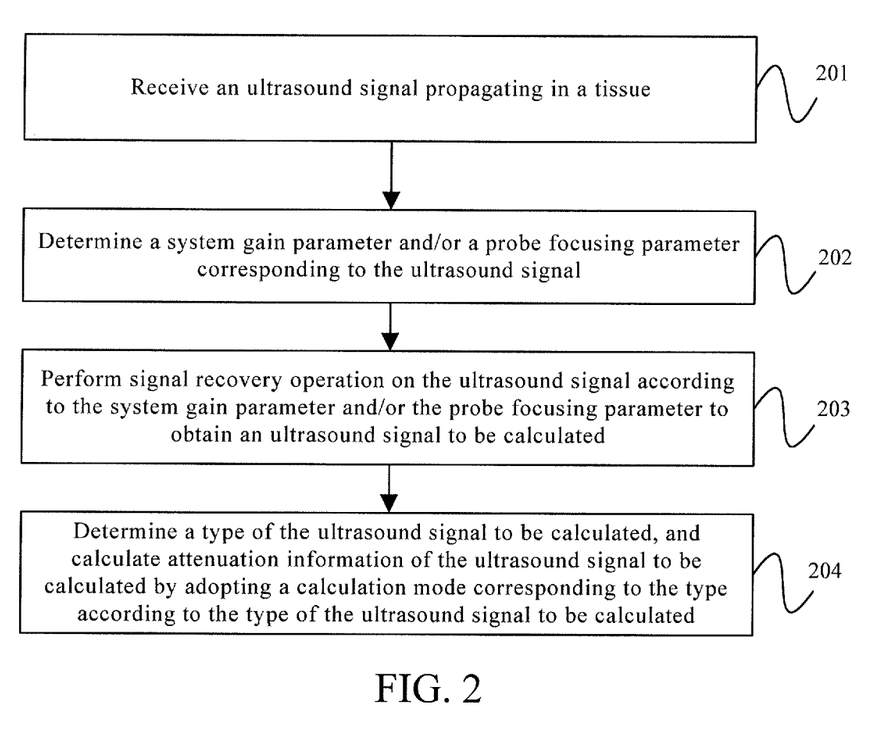
FIG. 2 is a schematic flowchart of a method for calculating signal attenuation according to Embodiment 2 of the present disclosure.

FIG. 2 is a schematic flowchart of a method for calculating signal attenuation according to Embodiment 2 of the present disclosure. On the basis of any of the aforementioned embodiments, as shown in FIG. 2, the method comprises:

Step 201: receiving an ultrasound signal propagating in a tissue;

An ultrasound imaging system transmits an ultrasound signal, which is propagating in a tissue; and the ultrasound signal propagating in the tissue is then received by the ultrasound imaging system. The ultrasound signal may be an ultrasound reflection signal or an ultrasound transmission signal.

Step 202: determining a system gain parameter and/or a probe focusing parameter corresponding to the ultrasound signal;

Step 203: performing signal recovery operation on the ultrasound signal according to the system gain parameter and/or the probe focusing parameter to obtain an ultrasound signal to be calculated; and Step 204: determining a type of the ultrasound signal to be calculated, and calculating attenuation information of the ultrasound signal to be calculated by adopting a calculation mode corresponding to the type according to the type of the ultrasound signal to be calculated.

In this embodiment, settings, such as probe focusing or system gain, are usually adopted in order to focus on a partial region. As a result, attenuation information obtained by calculating an ultrasound signal based on probe focusing or system gain is often not accurate enough. In order to increase the accuracy of signal attenuation information, after the ultrasound signal is obtained, signal recovery operation needs to be performed on the ultrasound signal to obtain an ultrasound signal to be calculated. Specifically, it is necessary to determine the system gain parameter and/or the probe focusing parameter corresponding to the ultrasound signal first, and signal recovery operation is performed on the ultrasound signal according to the system gain parameter and/or the probe focusing parameter to obtain the ultrasound signal to be calculated. It is appreciated that subtraction or multiplication operation may be performed on the ultrasound signal according to the currently applied system gain parameter and/or probe focusing parameter to achieve the recovery of the ultrasound signal. Taking a practical application as an example, in order to focus on a partial region, a five-fold system gain parameter may be set, so that after an ultrasound signal is acquired, the ultrasound signal can be divided by five to achieve the recovery of the ultrasound signal. It is appreciated that the accuracy and efficiency of attenuation calculation can be increased by performing attenuation calculation subsequent to the recovery of the acquired ultrasound signal.

According to the method for calculating signal attenuation provided by this embodiment, the ultrasound signal to be calculated is obtained by determining a system gain parameter and/or a probe focusing parameter corresponding to the ultrasound signal and performing signal recovery operation on the ultrasound signal according to the system gain parameter and/or the probe focusing parameter. Thereby, the signal attenuation calculation flow is simplified, enabling use of commercial probes therein, bringing convenience in operation, and increasing applicability. In addition, the accuracy and efficiency of attenuation calculation can be increased by performing attenuation calculation subsequent to the recovery of the acquired ultrasound signal.

Figure 3:
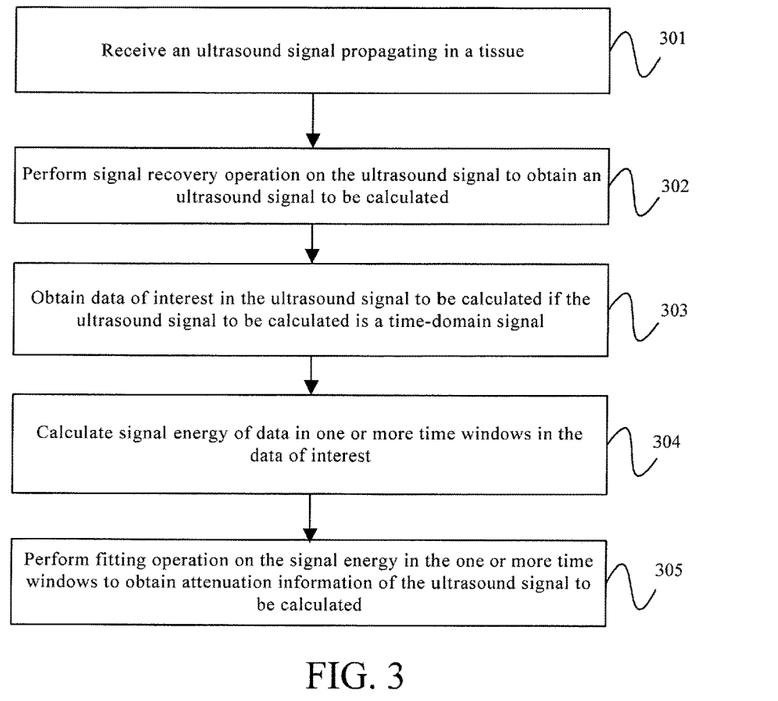
FIG. 3 is a schematic flowchart of a method for calculating signal attenuation according to Embodiment 3 of the present disclosure.

FIG. 3 is a schematic flowchart of a method for calculating signal attenuation according to Embodiment 3 of the present disclosure. On the basis of any of the aforementioned embodiments, as shown in FIG. 3, the method comprises:

Step 301: receiving an ultrasound signal propagating in a tissue;

Step 302: performing signal recovery operation on the ultrasound signal to obtain an ultrasound signal to be calculated;

Step 303: obtaining data of interest in the ultrasound signal to be calculated if the ultrasound signal to be calculated is a time-domain signal;

Step 304: calculating signal energy of data in one or more time windows in the data of interest; and Step 305: performing fitting operation on the signal energy in the one or more time windows to obtain attenuation information of the ultrasound signal to be calculated.

In this embodiment, in order to increase the efficiency of calculation, signal attenuation calculation may be performed on the data of interest of a region of interest in the ultrasound signal. After the ultrasound signal to be calculated is obtained, the type of the ultrasound signal to be calculated needs to be determined first. If the ultrasound signal to be calculated is a time-domain signal, data of interest in the ultrasound signal to be calculated is obtained, and signal energy of data in one or more time windows in the data of interest is calculated. It should be noted that, any method capable of implementing signal energy calculation may be adopted to implement the calculation of the signal energy of the data of interest, which is not limited herein. For example, the signal energy of the region of interest may be calculated by adopting an amplitude squaring method. After the signal energy intensity of the data of interest is obtained, fitting operation may be performed on the signal energy to obtain attenuation information of the ultrasound signal to be calculated.

It should be noted that if the current ultrasound signal is a signal of multiple lines, the signal of multiple lines may be divided into multiple blocks, attenuation information of each block is calculated separately, and an average value for the attenuation information of blocks is calculated to obtain attenuation information of the ultrasound signal. By dividing the ultrasound signal and then calculating the average value, the accuracy of calculating the attenuation information of the ultrasound signal can be increased.

According to the method for calculating signal attenuation provided by this embodiment, if the ultrasound signal to be calculated is a time-domain signal, the data of interest in the ultrasound signal to be calculated is obtained, signal energy of at least one section of the data of interest is calculated, and fitting operation is performed on the signal energy to obtain attenuation information of the ultrasound signal to be calculated, thereby realizing the calculation of the attenuation information of the time-domain ultrasound signal.

Figure 4:
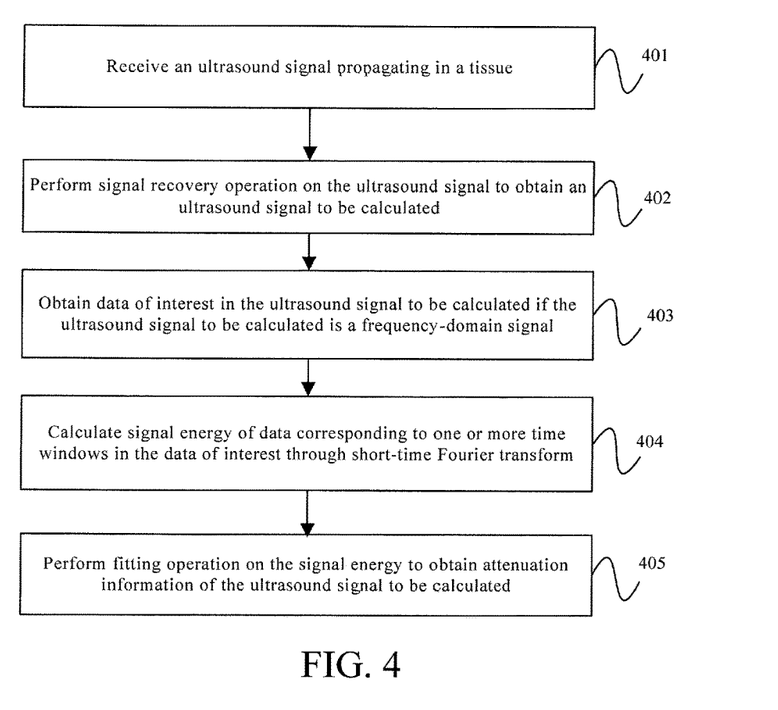
FIG. 4 is a schematic flowchart of a method for calculating signal attenuation according to Embodiment 4 of the present disclosure.

FIG. 4 is a schematic flowchart of a method for calculating signal attenuation according to Embodiment 4 of the present disclosure. On the basis of any of the aforementioned embodiments, the method comprises:

Step 401: receiving an ultrasound signal propagating in a tissue;

Step 402: performing signal recovery operation on the ultrasound signal to obtain an ultrasound signal to be calculated;

Step 403: obtaining data of interest in the ultrasound signal to be calculated if the ultrasound signal to be calculated is a frequency-domain signal;

Step 404: calculating signal energy of data corresponding to one or more time windows in the data of interest through short-time Fourier transform; and Step 405: performing fitting operation on the signal energy to obtain attenuation information of the ultrasound signal to be calculated.

In this embodiment, in order to increase the efficiency of calculation, signal attenuation calculation may be performed on the data of interest of a region of interest in the ultrasound signal. After the ultrasound signal to be calculated is obtained, the type of the ultrasound signal to be calculated needs to be determined first. If the ultrasound signal to be calculated is a frequency-domain signal, data of interest in the ultrasound signal to be calculated is obtained, and signal energy of at least one section of the data of interest is calculated. In particular, the signal energy of the data of interest may be calculated by short-time Fourier transform. After the signal energy intensity of the data of interest is obtained, fitting operation may be performed on the signal energy to obtain attenuation information of the ultrasound signal to be calculated.

According to the method for calculating signal attenuation provided by this embodiment, if the ultrasound signal to be calculated is a frequency-domain signal, the data of interest in the ultrasound signal to be calculated is obtained, signal energy of at least one section of the data of interest is calculated by short-time Fourier transform, and fitting operation is performed on the signal energy to obtain attenuation information of the ultrasound signal to be calculated, thereby realizing the calculation of the attenuation information of the frequency-domain ultrasound signal.

It should be noted that for different types of ultrasound signals, type conversion may be performed on the ultrasound signals, and the same calculation mode is adopted to calculate attenuation information for the converted ultrasound signals. Specifically, the frequency-domain signal may be converted into a time-domain signal or the time-domain signal may be converted into a frequency-domain signal, which is not limited herein.

Further, on the basis of any of the aforementioned embodiments, the performing fitting operation on the signal energy to obtain attenuation information of the ultrasound signal to be calculated comprises:

performing one-dimensional linear fitting and/or least square fitting and/or cubic spline fitting operation on the signal energy to obtain the attenuation information of the ultrasound signal to be calculated.

In this embodiment, the attenuation information of the ultrasound signal may be calculated by adopting a linear fitting method or a non-linear fitting method. For example, specifically, the attenuation information of the ultrasound signal to be calculated may be obtained by performing one-dimensional linear fitting and/or least square fitting and/or cubic spline fitting on the signal energy of the data of interest. In addition, other fitting algorithms may also be adopted to calculate the attenuation information of the ultrasound signal, which is not limited herein.

According to the method for calculating signal attenuation provided by this embodiment, the attenuation information of the ultrasound signal to be calculated is obtained by performing one-dimensional linear fitting and/or least square fitting and/or cubic spline fitting on the signal energy, so that the attenuation information of the ultrasound signal can be accurately calculated.

Figure 5:
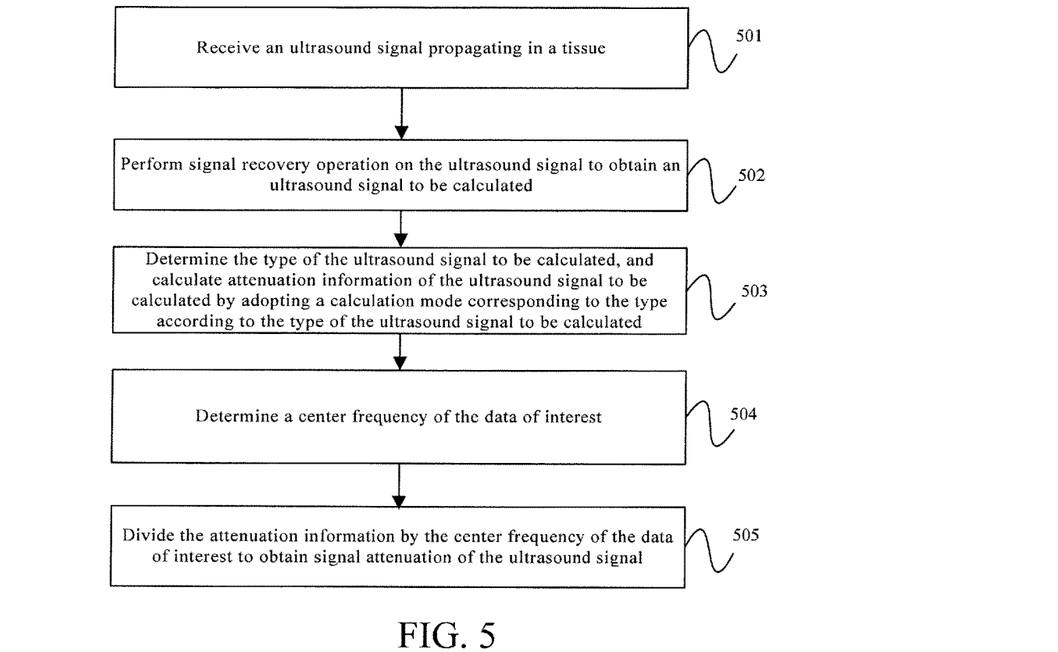
FIG. 5 is a schematic flowchart of a method for calculating signal attenuation according to Embodiment 5 of the present disclosure.

FIG. 5 is a schematic flowchart of a method for calculating signal attenuation according to Embodiment 5 of the present disclosure. On the basis of any of the aforementioned embodiments, as shown in FIG. 5, the method further comprises:

Step 501: receiving an ultrasound signal propagating in a tissue;

Step 502: performing signal recovery operation on the ultrasound signal to obtain an ultrasound signal to be calculated;

Step 503: determining a type of the ultrasound signal to be calculated, and calculating attenuation information of the ultrasound signal to be calculated by adopting a calculation mode corresponding to the type according to the type of the ultrasound signal to be calculated;

Step 504: determining a center frequency of the data of interest; and

Step 505: dividing the attenuation information by the center frequency of the data of interest to obtain signal attenuation of the ultrasound signal.

In this embodiment, after the attenuation information of the ultrasound signal is obtained by calculation, the attenuation information may be normalized to obtain the signal attenuation of the ultrasound signal. Specifically, the center frequency of the data of interest may be determined, and the signal attenuation of the ultrasound signal is calculated from the attenuation information and the center frequency of the data of interest. Specifically, the attenuation information of the ultrasound signal may be normalized by dividing the attenuation information by the center frequency of the data of interest. Taking a practical application as an example, if attenuation information of a signal of a region A is calculated as 100 dB/m, a center frequency of the signal of the region A is 2 MHz, attenuation information of a signal of a region B is 500 dB/m and a center frequency of the signal of the region B is 5 MHz, the attenuation information of each ultrasound signal is normalized by diving the attenuation information by the center frequency of the data of interest, so that the attenuation information of the signal of the region A can be determined as 50 dB/m/MHz and the attenuation information of the signal of the region B can be determined as 100 dB/m/MHz. In addition, by normalizing the attenuation information, the unit of each region in the ultrasound signal can be kept consistent, facilitating subsequent calculation and processing.

According to the method for calculating signal attenuation provided by this embodiment, by determining the center frequency of the data of interest and dividing the attenuation information by the center frequency of the data of interest, the signal attenuation of the ultrasound signal is obtained. Thus, the unit of each region in the ultrasound signal can be kept consistent, facilitating subsequent calculation and processing.

Figure 6:
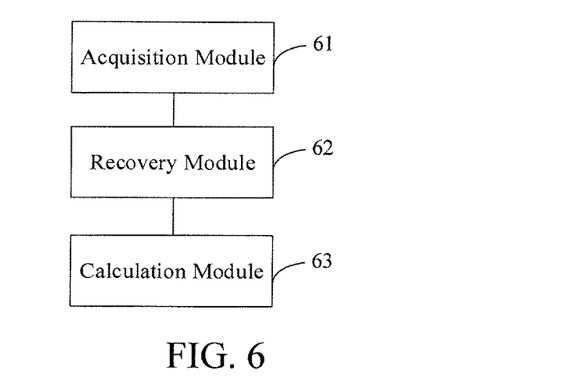
FIG. 6 is a schematic structural diagram of an apparatus for calculating signal attenuation according to Embodiment 6 of the present disclosure.

FIG. 6 is a schematic structural diagram of an apparatus for calculating signal attenuation according to Embodiment 6 of the present disclosure. As shown in FIG. 6, the apparatus comprises:

an acquisition module 61, configured for receiving an ultrasound signal propagating in a tissue;

a recovery module 62, configured for performing signal recovery operation on the ultrasound signal to obtain an ultrasound signal to be calculated; and a calculation module 63, configured for determining a type of the ultrasound signal to be calculated and calculating attenuation information of the ultrasound signal to be calculated by adopting a calculation mode corresponding to the type according to the type of the ultrasound signal to be calculated.

For an ultrasound signal, it is necessary to calculate attenuation thereof in order to carry out an analysis thereof. Therefore, the ultrasound signal for which attenuation information needs to be calculated needs to be acquired first, and particularly, the acquisition of the ultrasound signal may be implemented by an ultrasound imaging system. In order to focus on a partial region, generally, settings, such as probe focusing or system gain, are adopted. As a result, attenuation information obtained by calculating an ultrasound signal based on probe focusing or system gain is often not accurate enough. In order to increase the accuracy of signal attenuation information, after the ultrasound signal is obtained, signal recovery operation needs to be performed on the ultrasound signal to obtain an ultrasound signal to be calculated. It can be understood that there are two different types of ultrasound signals to be calculated, i.e. a time-domain signal and a frequency-domain signal. In order to ensure the accuracy of attenuation information calculation, different calculation modes should be adopted for respective different types of ultrasound signals to be calculated. Therefore, after an ultrasound signal to be calculated is obtained, the type of the ultrasound signal to be calculated needs to be determined first, then a calculation mode corresponding to the signal type is adopted according to the different types, and the ultrasound signal to be calculated is calculated by the calculation mode corresponding to the signal type, so that attenuation information corresponding to the ultrasound signal is obtained. Optionally, the ultrasound signal may be a one-dimensional ultrasound signal, a two-dimensional ultrasound signal or a three-dimensional ultrasound signal, which is not limited herein.

According to the apparatus for calculating signal attenuation provided by this embodiment, an ultrasound signal is acquired by an ultrasound imaging system; signal recovery operation is performed on the ultrasound signal to obtain an ultrasound signal to be calculated; the type of the ultrasound signal to be calculated is determined, and attenuation information of the ultrasound signal to be calculated is calculated by adopting a calculation mode corresponding to the type according to the type of the ultrasound signal to be calculated. Thereby, the signal attenuation calculation flow is simplified, enabling use of commercial probes therein, bringing convenience in operation, and increasing applicability. In addition, the accuracy and efficiency of attenuation calculation can be increased by performing attenuation calculation subsequent to the recovery of the acquired ultrasound signal.

Further, on the basis of any of the aforementioned embodiments, the recovery module comprises:
a determination unit, configured for determining a system gain parameter and/or a probe focusing parameter corresponding to the ultrasound signal; and
a recovery unit, configured for performing signal recovery operation on the ultrasound signal according to the system gain parameter and/or the probe focusing parameter to obtain the ultrasound signal to be calculated;

Further, on the basis of any of the aforementioned embodiments, the calculation module comprises:
a first acquisition unit, configured for obtaining data of interest in the ultrasound signal to be calculated if the ultrasound signal to be calculated is a time-domain signal;
a first calculation unit, configured for calculating signal energy of data in one or more time windows in the data of interest; and
a first fitting unit, configured for performing fitting operation on the signal energy in the one or more time windows to obtain the attenuation information of the ultrasound signal to be calculated.

Further, on the basis of any of the aforementioned embodiments, the calculation module comprises:
a second acquisition unit, configured for obtaining data of interest in the ultrasound signal to be calculated if the ultrasound signal to be calculated is a frequency-domain signal;
a second calculation unit, configured for calculating signal energy of data corresponding to one or more time windows in the data of interest through short-time Fourier transform; and
a second fitting unit, configured for performing fitting operation on the signal energy to obtain the attenuation information of the ultrasound signal to be calculated.

Further, on the basis of any of the aforementioned embodiments, the second fitting unit is specifically configured for:
performing one-dimensional linear fitting and/or least square fitting and/or cubic spline fitting operation on the signal energy to obtain the attenuation information of the ultrasound signal to be calculated.

Further, on the basis of any of the aforementioned embodiments, the apparatus further comprises:
a determination module, configured for determining a center frequency of the data of interest; and
a signal attenuation calculation module, configured for obtaining signal attenuation of the ultrasound signal by dividing the attenuation information by the center frequency of the data of interest.

Figure 7:
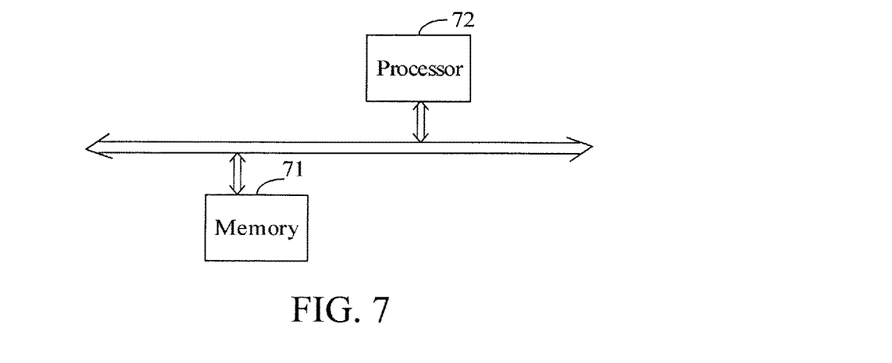
FIG. 7 is a schematic structural diagram of a device for calculating signal attenuation according to Embodiment 7 of the present disclosure.

FIG. 7 is a schematic structural diagram of a device for calculating signal attenuation according to Embodiment 7 of the present disclosure. As shown in FIG. 7, the device for calculating signal attenuation comprises: a memory 71 and a processor 72, wherein
the memory 71 is configured for storing instructions executable by the processor 72; and
the processor 72 is configured for executing the method for calculating signal attenuation according to any of the aforementioned embodiments.

Yet another embodiment of the present disclosure further provides a computer-readable storage medium having computer-executable instructions stored thereon, wherein the computer-executable instructions are used to implement the method for calculating signal attenuation according to any of the aforementioned embodiments when executed by a processor.

It can be clearly understood by those skilled in the art that for convenience and simplicity of description, the specific operating process of the apparatus described above may refer to the corresponding process in the foregoing method embodiments, which will not be repeated here.

Those of ordinary skill in the art will understand that all or part of the steps of implementing each aforementioned method embodiment may be carried out by hardware associated with program instructions. The aforementioned program may be stored in a computer-readable storage medium. When the program is executed, the steps of each aforementioned method embodiment are executed; and the aforementioned storage medium includes various media that can store program codes, such as a ROM, a RAM, a magnetic disk or an optical disk.

Finally, it should be noted that, the above embodiments are only used to illustrate, rather than limit, the technical solutions of the present disclosure; although the present disclosure is described in detail with reference to the embodiments described above, it will be understood by those skilled in the art that, the technical solutions in the embodiments described above can still be modified, or some or all of the technical features can be equivalently replaced; and these modifications or replacements do not make the technical solutions corresponding thereto depart from the scope of the technical solutions in the embodiments of the present disclosure.

The invention claimed is:

1. A method for calculating signal attenuation, comprising:
receiving an ultrasound signal propagating in a tissue by an ultrasound imaging system;
performing a signal recovery operation on the ultrasound signal propagating in a tissue to obtain a recovered ultrasound signal; and
determining a type of the recovered ultrasound signal, wherein the type of the recovered ultrasound signal is either a time-domain signal or a frequency-domain signal, and calculating attenuation information of the recovered ultrasound signal by adopting a calculation mode corresponding to the type according to the type of the recovered ultrasound signal so as to achieve signal attenuation calculation by use of a commercial probe,
wherein performing the signal recovery operation on the ultrasound signal propagating in the tissue to obtain a recovered ultrasound signal comprises:

determining a system gain parameter and a probe focusing parameter corresponding to the ultrasound signal propagating in a tissue; and performing the signal recovery operation on the ultrasound signal propagating in the tissue according to the system gain parameter and the probe focusing parameter to obtain the recovered ultrasound signal, wherein determining the type of the recovered ultrasound signal and calculating attenuation information of the recovered ultrasound signal by adopting a calculation mode corresponding to the type according to the type of the recovered ultrasound signal comprises:

obtaining data of interest in the recovered ultrasound signal if the recovered ultrasound signal is the time-domain signal;

calculating signal energy of data in one or more time windows in the data of interest; and performing a fitting operation on the signal energy in the one or more time windows to obtain the attenuation information of the recovered ultrasound signal, and wherein determining the type of the recovered ultrasound signal and calculating attenuation information of the recovered ultrasound signal by adopting a calculation mode corresponding to the type according to the type of the recovered ultrasound signal further comprises:

obtaining data of interest in the recovered ultrasound signal if the recovered ultrasound signal is the frequency-domain signal;

calculating signal energy of data corresponding to one or more time windows in the data of interest through short-time Fourier transform; and performing a fitting operation on the signal energy to obtain the attenuation information of the recovered ultrasound signal.

2. The method according to claim 1, wherein performing the fitting operation on the signal energy to obtain the attenuation information of the recovered ultrasound signal comprises:

performing a one-dimensional linear fitting and/or least square fitting and/or cubic spline fitting operation on the signal energy to obtain the attenuation information of the recovered ultrasound signal.

3. The method according to claim 1, wherein after the determining the type of the recovered ultrasound signal and calculating attenuation information of the recovered ultrasound signal by adopting a calculation mode corresponding to the type according to the type of the recovered ultrasound signal, the method further comprises:

determining a center frequency of the data of interest; and dividing the attenuation information by the center frequency of the data of interest to obtain signal attenuation of the recovered ultrasound signal.

4. A non-transitory computer-readable storage medium having computer-executable instructions stored thereon, wherein the computer-executable instructions are used to implement the method for calculating signal attenuation according to claim 1 when executed by a processor.

5. An apparatus for calculating signal attenuation, comprising:

an acquisition module, configured for receiving an ultrasound signal propagating in a tissue by an ultrasound imaging system;

a recovery module, configured for performing a signal recovery operation on the ultrasound signal propagating in a tissue to obtain a recovered ultrasound signal; and a calculation module, configured for determining a type of the recovered ultrasound signal, wherein the type of the recovered ultrasound signal is either a time-domain signal or a frequency-domain signal, and calculating attenuation information of the recovered ultrasound signal by adopting a calculation mode corresponding to the type according to the type of the recovered ultrasound signal so as to achieve signal attenuation calculation by use of a commercial probe, wherein the recovery module comprises:

a determination unit, configured for determining a system gain parameter and a probe focusing parameter corresponding to the ultrasound signal propagating in a tissue; and a recovery unit, configured for performing the signal recovery operation on the ultrasound signal propagating in the tissue according to the system gain parameter and the probe focusing parameter to obtain the recovered ultrasound signal, wherein the calculation module comprises:

a first acquisition unit, configured for obtaining data of interest in the recovered ultrasound signal if the recovered ultrasound signal is the time-domain signal;

a first calculation unit, configured for calculating signal energy of data in one or more time windows in the data of interest; and a first fitting unit, configured for performing a fitting operation on the signal energy in the one or more time windows to obtain the attenuation information of the recovered ultrasound signal, and wherein the calculation module comprises:

a second acquisition unit, configured for obtaining data of interest in the recovered ultrasound signal if the recovered ultrasound signal is the frequency-domain signal;

a second calculation unit, configured for calculating signal energy of data corresponding to one or more time windows in the data of interest through short-time Fourier transform; and a second fitting unit, configured for performing a fitting operation on the signal energy to obtain the attenuation information of the recovered ultrasound signal.

6. The apparatus according to claim 5, wherein the second fitting unit is specifically configured for:

performing a one-dimensional linear fitting and/or least square fitting and/or cubic spline fitting operation on the signal energy to obtain the attenuation information of the recovered ultrasound signal.

7. The apparatus according to claim 5, further comprising:

a determination module, configured for determining a center frequency of the data of interest; and a signal attenuation calculation module, configured for obtaining signal attenuation of the recovered ultrasound signal by dividing the attenuation information by the center frequency of the data of interest.

* * * * *